US009265868B2

(12) United States Patent
Cheng

(10) Patent No.: US 9,265,868 B2
(45) Date of Patent: Feb. 23, 2016

(54) AUTOMATIC FAT REMOVAL DEVICE

(71) Applicant: Ming-Huei Cheng, Taipei (TW)

(72) Inventor: Ming-Huei Cheng, Taipei (TW)

( * ) Notice: Subject to any disclaimer, the term of this patent is extended or adjusted under 35 U.S.C. 154(b) by 159 days.

(21) Appl. No.: 13/871,095

(22) Filed: Apr. 26, 2013

(65) Prior Publication Data
US 2013/0289535 A1 Oct. 31, 2013

(30) Foreign Application Priority Data

Apr. 27, 2012 (TW) .............................. 101115157 A

(51) Int. Cl.
*A61M 1/00* (2006.01)
*A61B 17/34* (2006.01)
*A61B 19/00* (2006.01)
*A61B 5/15* (2006.01)
*A61B 17/00* (2006.01)

(52) U.S. Cl.
CPC ............ *A61M 1/008* (2013.01); *A61B 17/3403* (2013.01); *A61B 19/2203* (2013.01); *A61B 5/150816* (2013.01); *A61B 2017/003* (2013.01); *A61B 2019/2207* (2013.01); *A61B 2019/2211* (2013.01); *A61B 2019/2292* (2013.01); *A61B 2019/5231* (2013.01); *A61M 2202/08* (2013.01)

(58) Field of Classification Search
CPC ................... A61B 19/2203; A61B 2019/5231; A61B 2019/2207; A61B 2019/2211; A61B 19/50; A61B 17/32002; A61B 2017/320024; A61B 19/22; A61B 2017/320028; A61B 2017/320032; A61B 2017/320044; A61B 2017/320052; A61B 2018/00458; A61B 2018/00464; A61B 2019/2215; A61B 2019/2292; A61B 2019/2296; A61B 2019/465; A61B 5/0084; A61B 5/0205; A61B 5/042; A61B 17/3403; A61B 17/3476; A61B 17/003; A61B 2019/464; A61B 5/6885; A61B 2017/003; A61B 2019/2226; A61B 5/150816; A61B 5/7455; A61M 25/01; A61M 25/0102; A61M 25/09; A61M 25/09016; A61M 25/09025; A61M 2210/04; A61M 2210/1007; A61M 2210/1021; A61M 1/008; A61M 2202/08; A61M 1/0023; A61M 1/0039; A61M 2202/0014; A61M 25/0113; A61M 25/0116; A61M 25/04; A61M 2025/0293; A61M 25/0105
See application file for complete search history.

(56) References Cited

U.S. PATENT DOCUMENTS

| | | | | | |
|---|---|---|---|---|---|
| 4,957,482 | A | * | 9/1990 | Shiber | 604/22 |
| 5,123,903 | A | * | 6/1992 | Quaid et al. | 604/22 |
| 5,472,416 | A | * | 12/1995 | Blugerman et al. | 604/28 |
| 6,120,519 | A | * | 9/2000 | Weber et al. | 606/170 |
| 6,159,176 | A | * | 12/2000 | Broadwin et al. | 604/22 |
| 2002/0029054 | A1 | * | 3/2002 | Rabiner et al. | 606/169 |
| 2002/0116043 | A1 | * | 8/2002 | Garibaldi et al. | 607/126 |
| 2002/0138021 | A1 | * | 9/2002 | Pflueger | 600/565 |
| 2003/0055360 | A1 | * | 3/2003 | Zeleznik | A61B 5/02007 600/587 |
| 2003/0088235 | A1 | * | 5/2003 | Tazi | 604/542 |

(Continued)

*Primary Examiner* — Adam Marcetich
(74) *Attorney, Agent, or Firm* — Bacon & Thomas, PLLC

(57) ABSTRACT

The present invention relates to a fat removal device, which comprises: a navigation system having a first connection end and a first terminal; a hollow suction tube having a second connection end and a second terminal, wherein the navigation system is disposed inside the hollow suction tube; a connection unit connected to the first connection end and the second connection end; a robotic arm connected to the connection unit to rotate and move the connection unit multidirectionally; a suction unit connected to the connection unit by a pipeline between the connection unit and the suction unit; and a microprocessor connected to the connection unit, the robotic arm, and the suction unit, to transmit signals from one to another.

11 Claims, 5 Drawing Sheets

(56) References Cited

U.S. PATENT DOCUMENTS

| | | | |
|---|---|---|---|
| 2003/0225364 A1* | 12/2003 | Kraft et al. ............ | 604/35 |
| 2006/0161045 A1* | 7/2006 | Merril ............ | A61B 1/018 600/117 |
| 2006/0206134 A1* | 9/2006 | Conquergood et al. ....... | 606/180 |
| 2007/0197939 A1* | 8/2007 | Wallace et al. ........... | 600/587 |
| 2008/0234708 A1* | 9/2008 | Houser et al. ........... | 606/169 |
| 2008/0269722 A1* | 10/2008 | Andrew et al. ........... | 604/542 |
| 2009/0221991 A1* | 9/2009 | Lieponis ............ | 604/540 |
| 2009/0275970 A1* | 11/2009 | Leibowitz ............ | 606/185 |
| 2010/0094267 A1* | 4/2010 | Ference et al. ............ | 606/15 |
| 2010/0280496 A1* | 11/2010 | Shippert ............ | 604/533 |
| 2011/0028898 A1* | 2/2011 | Clark, III ............ | A61B 18/1477 604/151 |
| 2011/0178508 A1* | 7/2011 | Ullrich ............ | 606/1 |
| 2011/0257661 A1* | 10/2011 | Choi et al. ............ | 606/130 |
| 2012/0116253 A1* | 5/2012 | Wallace et al. ........... | 600/587 |
| 2012/0130230 A1* | 5/2012 | Eichler ............ | A61B 17/22 600/424 |
| 2012/0157944 A1* | 6/2012 | Cucin ............ | 604/319 |
| 2012/0259311 A1* | 10/2012 | Hirshberg ........ | A61M 37/0015 604/506 |
| 2013/0012783 A1* | 1/2013 | Vayser et al. ............ | 600/249 |
| 2013/0190726 A1* | 7/2013 | Kesner ............ | A61M 25/0105 604/510 |

\* cited by examiner

AUTOMATIC FAT REMOVAL DEVICE

CROSS REFERENCE TO RELATED APPLICATION

This application claims the benefits of the Taiwan Patent Application Serial Number 101115157, filed on Apr. 27, 2012, the subject matter of which is incorporated herein by reference.

BACKGROUND OF THE INVENTION

1. Field of the Invention

The present invention relates to a fat removal device, and particularly to an automatic fat removal device which comprises a navigation system, a hollow suction tube, a connection unit, a robotic arm, a suction unit, and a microprocessor.

2. Description of Related Art

A typical method of fat removal surgery includes high frequency current fat disintegration, dermal-fat excision, ultrasonic fat disintegration, mechanical vibration, negative pressure suction, and so on.

Furthermore, dermal-fat excision, which directly excise extracts out the excess undesirable fat through a dermal incision, may cause scars, seroma, hematoma and infection.

Ultrasonic assisted fat removal device, fat cells is crushed by ultrasonic energy and extracted or extruded to outside of body by a negative pressure. However, such ultrasonic fat removal device takes more time and the probe temperature may be raised with the increased energy for fat disintegration. Sometimes, skin over the liposuction site is burned by the high-temperature probe.

Thus, negative pressure suction is the most widely-used fat removal surgery today, and the extracted fat may be used for materials of fat transplantation. However, a conventional liposuction device is operated at a single fixed point each time, and there is a variation in depth between each two liposuctions, and thus unevenness of skin development rise if the suction tube is too close to the skin.

Also, a reciprocating liposuction movement needed during a typical massive liposuction surgery is performed by a surgeon, and a considerable physical strength is required, resulting fatigue of the surgeon, which may cause more complications.

Therefore, in order to solve the above-mentioned problems, it is desirable to develop a fat removal device, which can advantageously improve the unevenness of skin during liposuction and relieve considerable physical and mental fatigue of the surgeon with assistance of a robotic arm during surgery.

SUMMARY OF THE INVENTION

Therefore, the present invention has been made to solve the above problems, and other technical problems that have yet to be resolved.

An object of the present invention is to provide an automatic fat removal device, wherein a navigation system and a hollow suction tube are employed to replace the conventional rigid suction tube to perform a 3-dimensional liposuction process in the adipose layer thereby improving cost effectiveness and surgical outcome.

Another object of the present invention is to provide an automatic fat removal device, which employs a robotic arm to replace manual effort of the surgeon during surgery to decrease the load of the surgeon.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENT

Figure 1A:
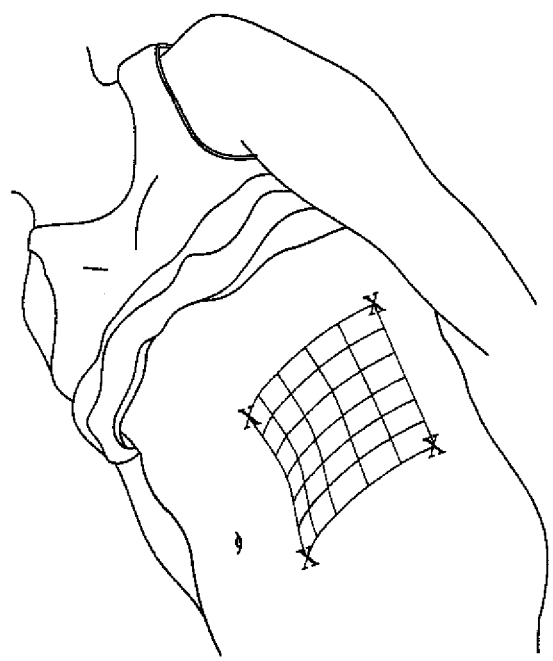
FIG. 1A illustrates a schematic view of the positioning and planning of the site for liposuction. The following steps were comprised: 1. Insert the positioning needles 80 (probes) to definite the area and depth of fat removal as shown in FIG. 1B; 2. Navigation system is used to start to scan the surface of area defined for fat removal; 3. Micro processer (chip) calculate and make a plan for fat removal, such as area, depth, speed, and required time; 4. Choose suction tube (large or small diameter with different side holes); 5. Set up the robotic system; 6. Action.
Figure 1B:
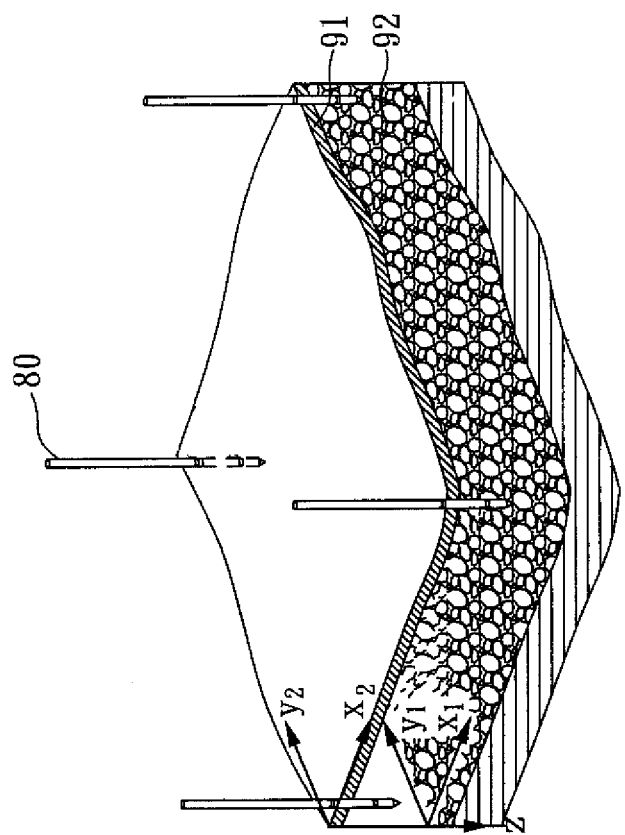
FIG. 1B is an enlarged schematic view of the site for liposuction.

In order to achieve to above objects, the present invention provides a automatic fat removal device, which comprises: a navigation system having a first connection end and a first terminal; a hollow suction tube having a second connection end and a second terminal, wherein the navigation system is disposed inside the hollow suction tube; a connection unit connected to the first connection end of the navigation system and the second connection end of the hollow suction tube; a robotic arm connected to the connection unit to rotate and move the connection unit multidirectionally; a suction unit connected to the connection unit by a pipeline between the connection unit and the suction unit; and a microprocessor connected to the connection unit, the robotic arm, and the suction unit, to transmit signals from one to another, wherein the hollow suction tube is used to perform fat removal in a direction guided by the navigation system in the adipose layer.

As mentioned above, the automatic fat removal device of the present invention may further comprise a storage unit for fat storage, and the location for the storage unit is not particularly limited as long as the function of extracted fat gathering can be achieved. Preferably, the storage unit is connected to the suction unit, and that is, the suction unit is disposed between the connection unit and the storage unit.

The navigation system of the present invention is used to guide the liposuction direction in advance during the liposuction process, and may be rod-shaped, circular, or tubular. In addition, the navigation system may be curved depending on various dermal conditions and body contour. Therefore, the navigation system may be formed of a resilient material, such as rubber, resin, or the like.

The hollow suction tube is used to extract fat by reciprocating movement in the direction guided by the navigation system, and thus also formed of a resilient material, such as rubber, resin, or the like. In addition, the second terminal of the hollow suction tube has an opening, and one or more side holes are on the tube wall of the second terminal. Although the number of the side holes shown in FIGs here are six, it is not limited thereto, and actually may be more than two, preferably 6 to 12, and more preferably 6 or more. Fat may be introduced into the automatic fat removal device of the present invention through the opening and the side holes. The navigation system guides in a fixed one-dimensional direction, and the hollow suction tube extracts fat positioned along this one-dimensional direction. After the liposuction in the one-dimensional direction is completed, another guiding and liposuction in another one-dimensional direction is performed. Then, after an liposuction of a predetermined plane is completed, liposuction of another plane located at a superficial position is performed. In this manner, the flatness of skin can be maintained after the liposuction surgery.

Furthermore, the connection unit of the present invention is connected to the first connection end of the navigation system and the second connection end of the hollow suction tube to affix the navigation system and the hollow suction tube.

Also, the robotic arm of the present invention is disposed on the connection unit to control the manner of movement and rotation of the connection unit. Thereby, the robotic arm may also adjust the operation process of direction alteration, movement, and rotation of the navigation system and the hollow suction tube.

Also, the suction unit can provide a negative pressure to the hollow suction tube, the connection unit, and the pipeline, and thus, the fat can be introduced from the adipose layer into the automatic fat removal device by the negative pressure. However, the suction unit may be any known suction units capable of providing suction function, such as a pump.

Also, the present invention provides a microprocessor connected to the navigation system, the hollow suction tube, the connection unit, the robotic arm, and the suction unit in a wireless or wired manner, thereby controlling the operation process of the automatic fat removal device to achieve the automatic liposuction. According to the present invention, the microprocessor further comprises a navigation system which may be a three-dimensional scanner, an ultrasonic detector, a photosensor, a thermal sensor, a camera, or the like, to control the operation status of the whole automatic fat removal device. A conventional three-dimensional scanner and an ultrasonic detector are preferably used as the sensing unit to provide image information, determine the direction of the position as well as the depth and thickness of the adipose layer, thereby determining the position to be subjected to the surgery. The signals transmitted between different units are further processed by the microprocessor to transmit instruction and control the movement and rotation of the robotic arm, the operation manners of the liposuction of the introducing pipeline connected to the connection unit and the hollow suction tube in the adipose layer, and the switch and rate of the suction unit.

Also, the automatic fat removal device according to the present invention may further comprise a power supply unit, wherein the power supply unit may be an external power supply unit which may connect to a power supply through a wire extended from the automatic fat removal device. In addition, the power supply unit may also be a power supply unit built in the automatic fat removal device such as a battery.

Furthermore, the present invention also provide a fat removal module, comprising: a navigation system having a first connection end and a first terminal; a hollow suction tube having a second connection end and a second terminal, wherein the navigation system is disposed inside the hollow suction tube; a connection unit connected to the first connection end of the navigation system and the second connection end of the hollow suction tube; wherein a liposuction process is performed in a straightforward one-dimensional direction by guiding the liposuction direction of the hollow suction tube with the navigation system, to improving flatness of skin surface.

In an embodiment, the navigation system according to the present invention may include a camera, a wireless unit (e.g. radio frequency or blue tooth), or a processor to position the probes more precisely, and then a series of electrical signals may be obtained by the camera, processed by the processor, and transmitted through the wireless unit. Such that, the area and depth for fat removal thus be defined, and then the robotic system with particular size and the number of the side hole may be calculated and planed by using the series of electrical signals to do liposuction.

Before the surgery is performed, fat position should be investigated with a computer tomography (CT) system or a digital camera to determine the area for liposuction. After characteristics of the internal structure of an object such as dimensions, shape, internal defects, and density are readily available from CT images, or appearance images are obtained from the camera, these obtained images are processed by a computer programming for 3D image modeling, or 3D surface topology. The robotic arm automatically moves to the specific position in 3 directions: latitudinal direction, longitudinal direction, and transverse direction (horizontal direction) according to the obtained 3D surface topology of a computer programming.

In addition, the automatic fat removal device according to the present invention may be operated combining with a robotic system to further overcome the limitations of both traditional open surgery and conventional minimally invasive surgery and improve the effect of the automatic fat removal device. The robotic System is a sophisticated robotic platform designed to expand the surgeon's capabilities and offer a minimally invasive option for major surgery. With this invented device, small incisions are used to introduce automatic liposuction cannula instruments under software control.

In the present invention, according to the obtained 3D surface topology of a computer programming and the obtained area, the thickness and the volume, a specific layer number, number of subcutaneous sites, positions of subcutaneous sites, a moving speed of a hollow suction tube in the adipose layer, and quantity/time for the liposuction surgery can be calculated automatically by computer programming. In result, the liposuction using the automatic fat removal device of the present invention is automatically performed in the form of stratification with a specific layer number, number of subcutaneous sites, positions of subcutaneous sites, a moving speed of a hollow suction tube in the adipose layer, and quantity/time by computer programming, wherein the liposuction at each of the subcutaneous sites in the same layer may scan a set area, and fat in these areas thus be removed automatically.

Embodiment 1

Figure 2:
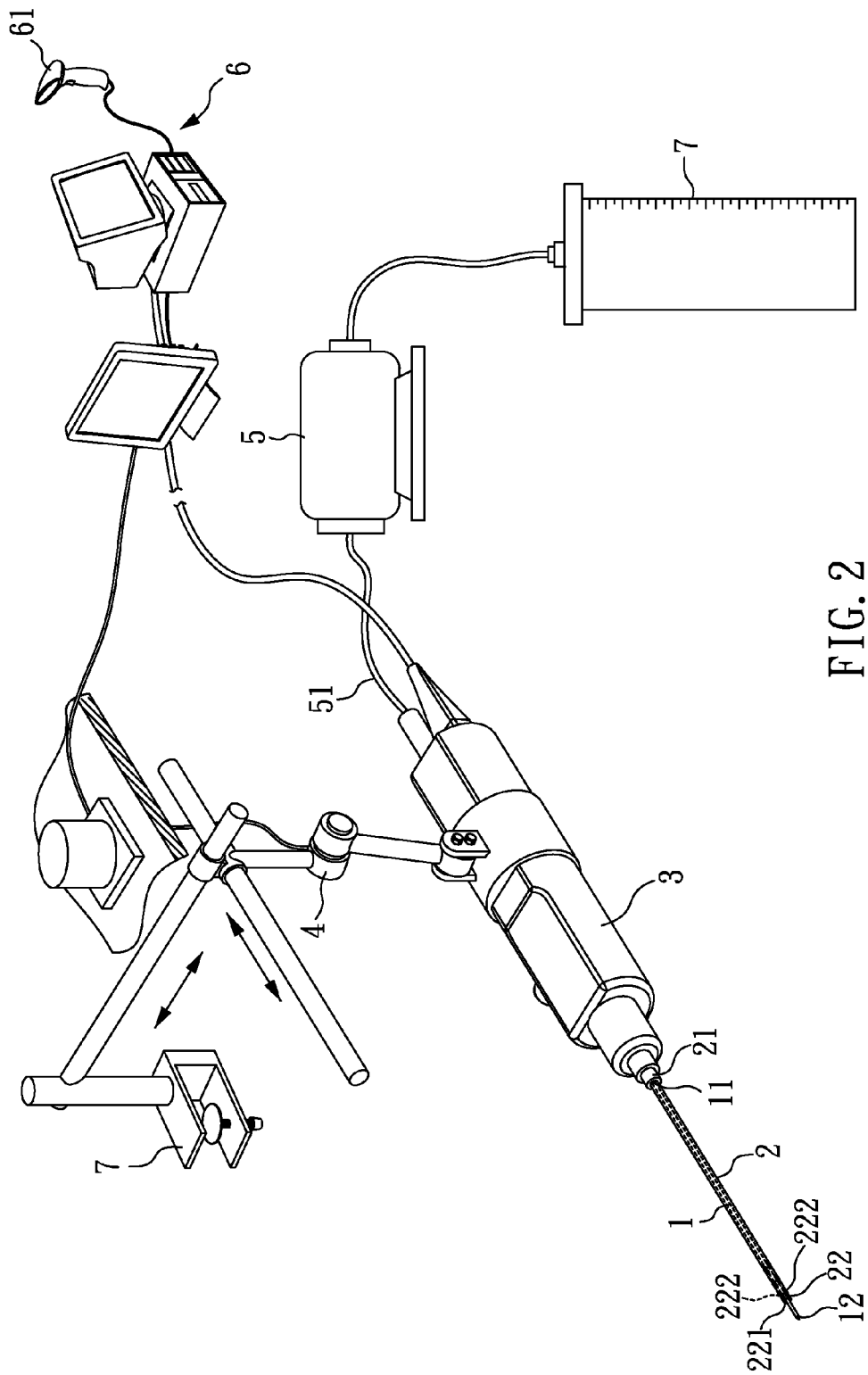
FIG. 2 shows a schematic view of the automatic fat removal device according to Embodiment 1 of the present invention. The automatic fat removal device of the present invention comprises a detecting probe 1, a hollow suction tube 2, a connection unit 3, a robotic arm 4 with 2-dimensional movement, and one operation table fixation 7, a suction unit 5, a microprocessor 6, and a power supply unit (not shown), wherein the navigation system 1 has a first connection end 11 and a first terminal 12, and the hollow suction tube 2 has a second connection end 21 and a second terminal 22.

Referring to FIG. 2, which shows a schematic view of the automatic fat removal device according to Embodiment 1 of the present invention. The automatic fat removal device of the present invention comprises a navigation system 1, a hollow suction tube 2, a connection unit 3, a robotic arm 4 with 2-dimensional movement, and one operation table fixation 7, a suction unit 5, a microprocessor 6, and a power supply unit (not shown), wherein the navigation system 1 has a first connection end 11 and a first terminal 12, and the hollow suction tube 2 has a second connection end 21 and a second terminal 22. In addition, the navigation system 1 is disposed inside the hollow suction tube, and the connection unit 3 is connected to the first connection end 11 of the navigation system 1 and the second connection end 21 of the hollow suction tube 2. As such, the navigation system 1 and the hollow suction tube 2 can be affixed to the connection unit 3 which may serve as a holder component. The navigation system 1 is formed of a resilient rod-shaped resin material, and the hollow suction tube 2 was formed of a resilient resin material, stainless steel, or titanium alloys. In addition, the second terminal 22 of the hollow suction tube 2 has an opening 221, and there are six side holes 222 which are left-right symmetric to each other on the tube wall of the second terminal. The fat in the adipose layer may be sucked into the automatic fat removal device of the present invention through the opening 221 and the side holes 222. The installation of the side holes 222 may increase the liposuction efficiency. Furthermore, the power supply unit (not shown) can provide an electric power source to the automatic fat removal device.

In this Embodiment, the robotic arm 4 is connected to the connection unit 3 to rotate and move the connection unit 3, line by line, layer by layer according to X, Y axis. The robotic arm replaces manual operation and can adjust the position and angle of the connection unit 3, thereby adjusting the positions and angles of the navigation system 1 and the hollow suction tube 2 inserting into the skin.

In addition, the suction unit 5 in this Embodiment is connected to the connection unit 3 by a pipeline 51 between the connection unit 3 and the suction unit 5, wherein the suction unit 5 is a pump for providing a negative pressure into the pipeline 51, the connection unit 3, and the hollow suction tube 2, and thus, the fat can be introduced from the adipose layer into the automatic fat removal device by the negative pressure. Furthermore, the automatic fat removal device of the present invention further comprises a storage unit 7 disposed at the end opposite to the pipeline 51 of the suction unit 5 between the connection unit and the storage unit, and that is, the suction unit 5 is between the pipeline 51 and the storage unit 7. Thus, the fat extracted out from the adipose layer can be stored in the storage unit 7 for subsequent uses, such as autologous fat transplantation; or just simply discarded.

Furthermore, the microprocessor 6 of the present Embodiment is electrically connected to the navigation system 1, the hollow suction tube 2, the connection unit 3, the robotic arm 4, and the suction unit 5, and the microprocessor 6 further comprises a sensing unit 61 which is a three-dimensional scanner. Positioning and confirming of depth and thickness of the fat is performed by the three-dimensional scanner to transmit the image signal to the microprocessor 6, and then the microprocessor 6 is electrically connected to each component and sends instruction to control the movement position and rotation angle of the robotic arm 4. After the position and angle are determined, the operation of the connection unit 3 is performed by driving the navigation system 1 and the hollow suction tube 2 connected to the connection unit 3 into the subcutaneous fat.

Figure 3:
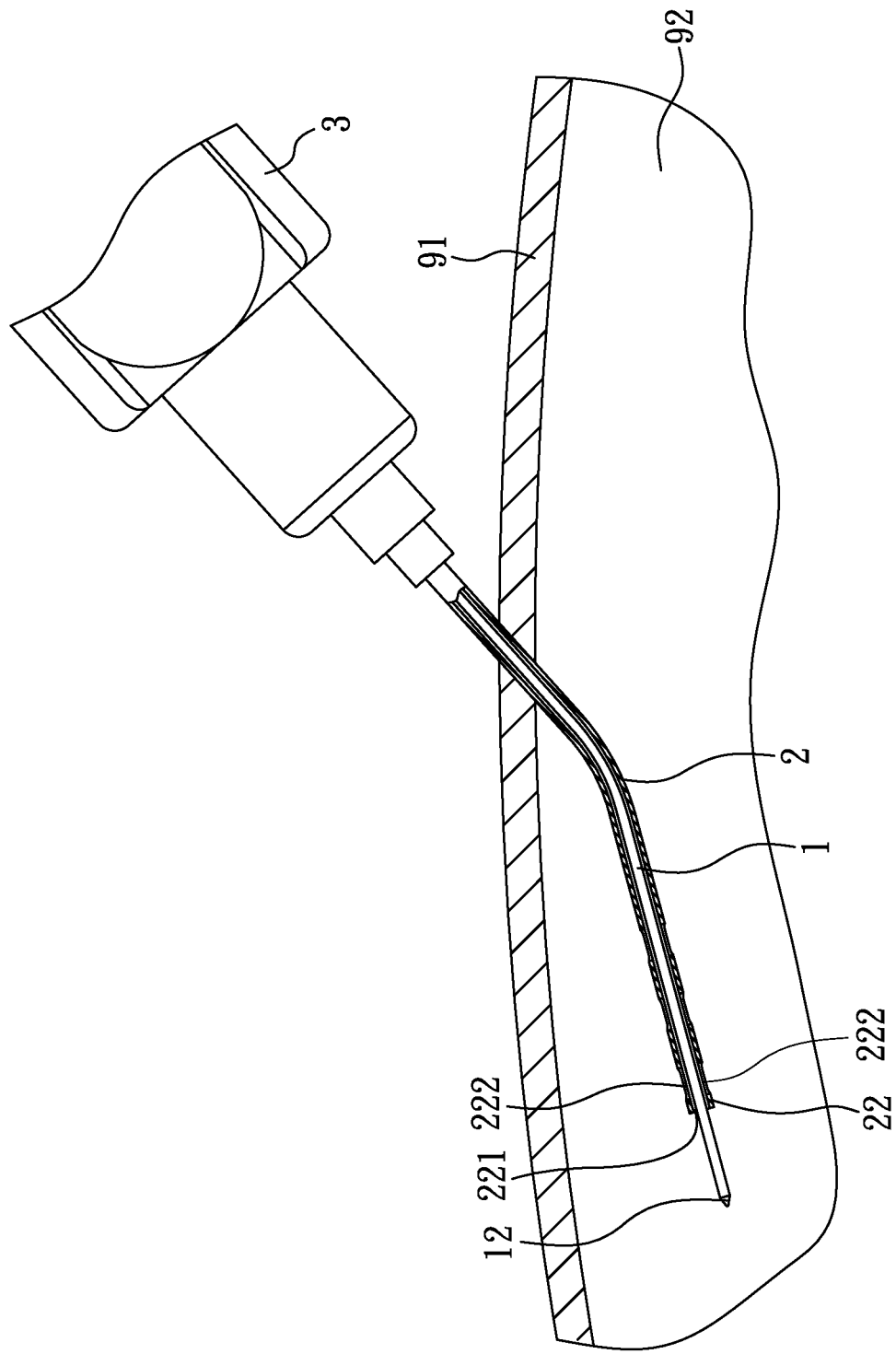
FIG. 3 illustrates the operation manner of the hollow suction tube according to the present invention. First, the operation is performed through the dermal layer 91 into the adipose layer 92, and the detecting probe 1 leads a processing route and a direction in the adipose layer 92. Then, the hollow suction tube 2 extracts fat by a reciprocating movement along the processing route and direction, wherein the fat in the adipose layer 92 is sucked into the automatic fat removal device of the present invention through the opening 221 and the side holes 222.

FIG. 3 illustrates the operation manner of the navigation system 1 and the hollow suction tube 2 according to the present invention. First, the operation is performed through the dermal layer 91 into the adipose layer 92, and the navigation system 1 leads a processing route and a direction in the adipose layer 92. Then, the hollow suction tube 2 extracts fat by a reciprocating movement along the processing route and direction, wherein the fat in the adipose layer 92 is sucked into the automatic fat removal device of the present invention through the opening 221 and the side holes 222. As such, the liposuction in one-dimensional direction is completed smoothly, and the flatness of skin can be maintained after the liposuction surgery.

This Embodiment may achieve liposuction for a large area and a large amount of fat in an automatic manner to reduce manual effort and surgery time.

Embodiment 2

Figure 4:
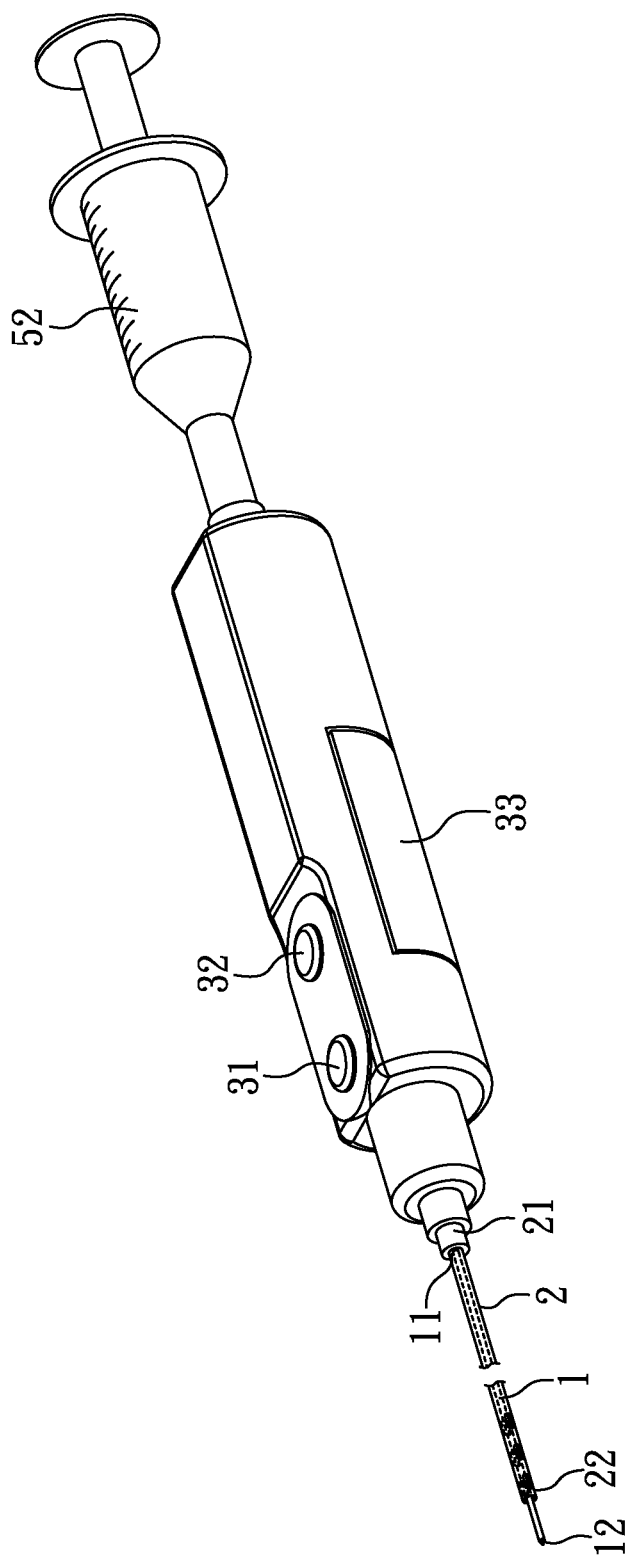
FIG. 4 shows a schematic view of the fat removal module according to Embodiment 2 of the present invention. The fat removal module of the present invention comprises a detecting probe 1, a hollow suction tube 2, and a connection unit 3, wherein the navigation system 1 has a first connection end 11 and a first terminal 12, and the hollow suction tube 2 has a second connection end 21 and a second terminal 22.

Referring to FIG. 4, which shows a schematic view of the fat removal module according to Embodiment 2 of the present invention. The fat removal module of the present invention comprises a navigation system 1, a hollow suction tube 2, and a connection unit 3, wherein the navigation system 1 has a first connection end 11 and a first terminal 12, and the hollow suction tube 2 has a second connection end 21 and a second terminal 22. In addition, the navigation system 1 is disposed inside the hollow suction tube, and the connection unit 3 is connected to the first connection end 11 of the navigation system 1 and the second connection end 21 of the hollow suction tube 2.

First, the navigation system 1 is inserted into a predetermined liposuction incision, and then the navigation system 1 is manipulated by a push-button navigation system adjusting element 31 to guide the processing route and direction in the adipose layer. Next, the hollow suction tube 2 is manipulated by a push-button hollow suction tube adjusting element of the speed (times/min) 32 to extract fat by reciprocating movement following the navigation system 1. As such, the liposuction process in one-dimensional direction can be achieved smoothly.

In addition, the navigation system 1 is formed of a resilient needle-shaped resin material, and the hollow suction tube 2 is formed of a resilient resin material, and the connection unit 3 is a rigid material serving as a holding component for users. In addition, the power supply source of this Embodiment is a battery 33.

The connection unit 3 may further comprise a suction syringe 52, and the fat in the adipose layer can be extracted and stored in the suction syringe 52 for subsequent uses, such as autologous fat transplantation. Nevertheless, this Embodiment may be applied to a liposuction of a small area and a small amount of fat, and the extracted amount can be controlled manually.

Embodiment 3

Figure 5:
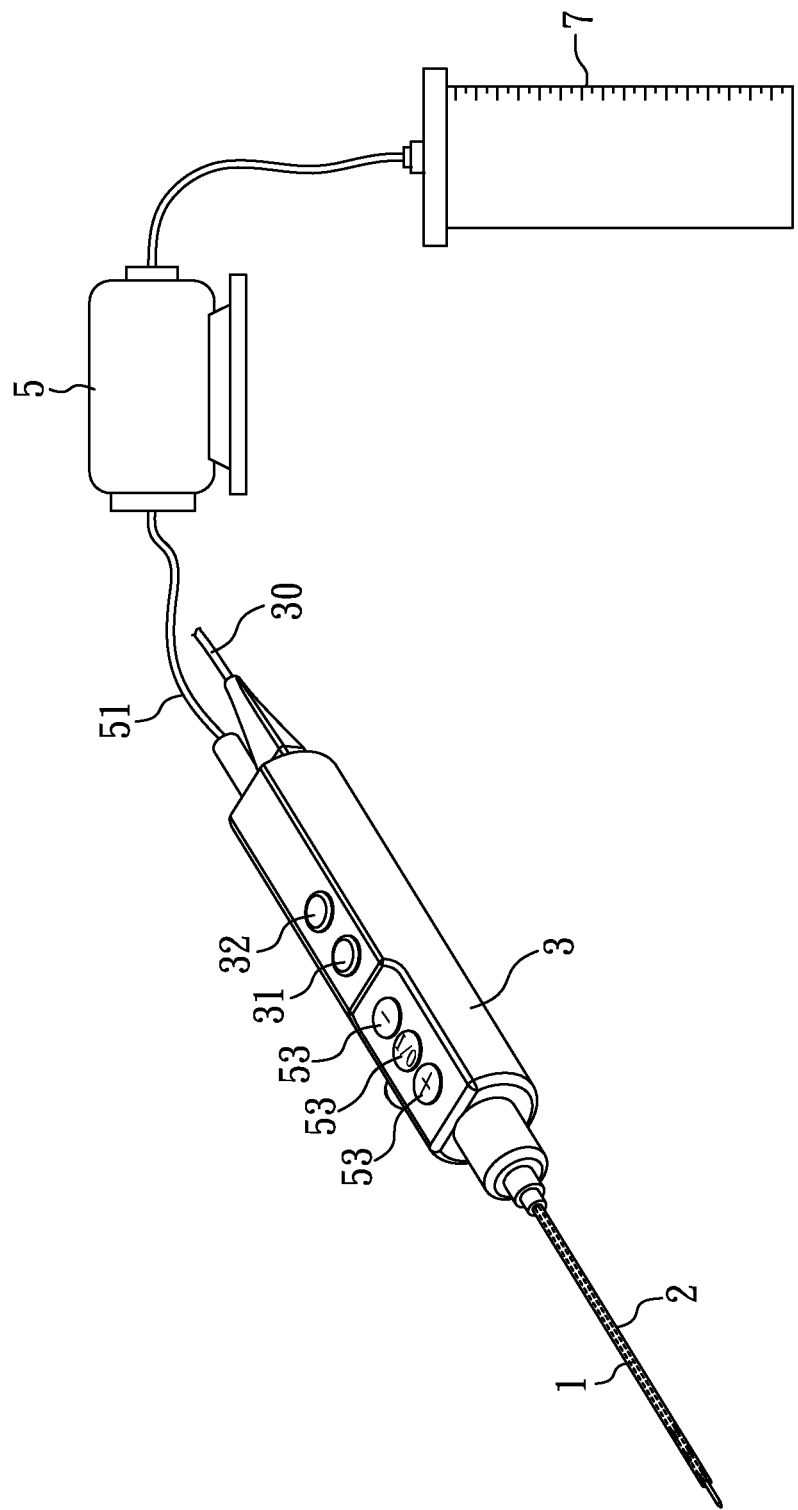
FIG. 5 shows a schematic view of the fat removal module according to Embodiment 3 of the present invention. The switch of the suction unit 5 is controlled in a form of push-button by a suction unit controlling element 53 installed on the connection unit 3 to adjust the rate of the suction unit 5. The suction unit controlling element 53 is a combination of push-buttons comprising a switch button, an acceleration button, and a deceleration button, and is electrically connection to the suction unit 5. In addition, the connection unit 3 of the present Embodiment is connected to a wire 30 extending to a power supply unit (not shown) to provide the electric power source of the present Embodiment.

Referring to FIG. 5, which shows a schematic view of the fat removal module according to Embodiment 3 of the present invention. The fat removal module of the present Embodiment is approximately the same as Embodiment 2 except that the suction unit 5 connected to the connection unit 3 is a pump. Thus, the switch of the suction unit 5 is controlled in a form of push-button by a suction unit controlling element 53 installed on the connection unit 3 to adjust the rate of the suction unit 5. The suction unit controlling element 53 is a combination of push-buttons comprising a switch button, an acceleration button, and a deceleration button, and is electrically connection to the suction unit 5. In addition, the connection unit 3 of the present Embodiment is connected to a wire 30 extending to a power supply unit (not shown) to provide the electric power source of the present Embodiment.

In this Embodiment, the liposuction process is performed in a semi-automatic manner, and the insertion positions, angles, and depths of the navigation system 1 and the hollow suction tube 2 are determined manually, such as in the face, neck area. Then, the navigation system 1 is manipulated by a push-button navigation system adjusting element 31 to guide the processing route and direction in the adipose layer. Next, the hollow suction tube 2 was manipulated by a push-button hollow suction tube adjusting element 32 to extract fat by reciprocating movement following the navigation system 1. Thus, the liposuction process in one-dimensional direction can be achieved smoothly. Moreover, the suction unit 5 is controlled by the suction unit controlling element 53 to provide a negative pressure for liposuction instead of manual liposuction.

The present Embodiment may ease the patient's discomfort caused by the noise from the robotic arm if patient is under local anesthesia, and may also reduce the manual effort of the surgeon during a surgery.

In this Embodiment, the second terminal 22 of the hollow suction tube 2 has an opening 221, and there are six side holes 222 which are left-right symmetric to each other on the tube wall of the second terminal. However, different types and numbers of the side holes may also be applied optionally. For example, the second terminal 22 of the hollow suction tube 2 has a plurality of through side 222 disposed around the tube wall, and each of the side holes 222 can be kept at same or different predetermined distances from the opening 221. Alternatively, the second terminal 22 of the hollow suction tube 2 has a plurality of side holes 222 disposed along the straight line extending in the direction of the hollow suction tube 2.

According to the above Embodiments, the layout of the navigation system 1 and the hollow suction tube 2 of the liposuction can solve the unevenness problem after a conventional negative pressure liposuction surgery, maintaining the flatness of skin.

Liposuction Process Flow

Anaesthesia Process

After the fat positioning process, a tumescent solution including physiological saline, local anaesthetics, hemostatics, and so on, for providing the effects of fat softening, analgesia, deswelling, and hemostasia, is injected to the site for liposuction. The above-mentioned process is called "aqua injection", preferably performed with massage for more complete penetration of medicine. In addition, a typical vibration, a waterjet, or an ultrasonication may then be used to crush the fat by breaking the fat cells with high frequency vibration, thereby emulsifying the fat into a liquid to facilitate the following liposuction process.

Liposuction

Then, the dermal layer is slit with a width of 0.5-1 cm, followed by inserting the automatic fat removal device of the present invention into the adipose layer for liposuction. For example, when using the automatic robotic arm of Embodiment 1 to perform the liposuction process, a liposuction process in the same depth is performed sequentially along the planned grid on the skin, and meanwhile, a sensing unit may be further installed onto the positioning needle, by which a signal is sent to the microprocessor when the navigation system of the automatic fat removal device is close to the sensing unit. Therefore, the navigation system of the automatic fat removal device can guide in the adipose layer without migrating to the muscle layer. After the liposuction of the predetermined plane (i.e. the area enclosed by the positioning needles) in the same depth is completed, a liposuction of the next plane is performed by using the robotic arm for regulation in height (for example, raising the navigation system and the hollow suction tube up to a predetermined height) according to the setting of the microprocessor. The fat with a volume of $[x \times y \times z \times (k-1)]$ can be sucked uniformly by the robotic arm and the computer processing to achieve the optimal liposuction effect in a time and effort-saving manner while reducing sequela such as unevenness or haemorrhage.

Nevertheless, the liposuction may also be performed by hand-holding the automatic fat removal device with a three-dimensional scanner, from one grid to another through the indication of the microprocessor. After the liposuction of the predetermined plane in the same depth is completed, then another liposuction of another plane in a different depth is performed, from deep to shallow, to complete a liposuction of a predetermined three-dimensional space.

In summary, the method for automatic fat removal according to the present invention may comprise the steps: first, insert the positioning needles (probes) to definite the area and depth of fat removal; and then, navigation system is used to start to scan the surface of area defined for fat removal followed by Microm processer (chip) calculation and planning for fat removal, such as area, depth, speed, and required time; after that, choose suction tube (large or small cahibers with different side holes); and finally set up the navigation of robotic system for suction automatically.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

Although the present invention has been explained in relation to its preferred embodiment, it is to be understood that many other possible modifications and variations can be made without departing from the spirit and scope of the invention as hereinafter claimed.

What is claimed is:

1. An automatic fat removal device, comprising:
   a navigation system having a first connection end and a first terminal, wherein the navigation system is formed of a resilient material which comprises at least one of rubber and resin;
   a hollow suction tube having a second connection end and a second terminal, wherein the navigation system is disposed inside the hollow suction tube;

a connection unit connected to the first connection end of the navigation system and the second connection end of the hollow suction tube;

a robotic arm connected to the connection unit to rotate and move the connection unit multidirectionally;

a suction unit connected to the connection unit by a pipeline between the connection unit and the suction unit;

a microprocessor connected to the connection unit, the robotic arm, and the suction unit, to transmit signals from one to another; and at least one positioning needle including a sensing unit connected to the microprocessor, wherein the hollow suction tube is used to perform fat removal in a direction guided by the navigation system in an adipose layer.

2. The fat removal device of claim 1, further comprising a storage unit connected to the suction unit for fat storage, wherein the suction unit is disposed between the connection unit and the storage unit connected to the suction unit.

3. The fat removal device of claim 1, wherein the navigation system is rod-shaped, acicular, or tubular.

4. The fat removal device of claim 1, wherein the hollow suction tube is formed of a resilient material.

5. The fat removal device of claim 1, wherein the second terminal of the hollow suction tube has an opening, and one or more side holes are on the tube wall of the second terminal.

6. The fat removal device of claim 5, wherein the second terminal of the hollow suction tube has six side holes.

7. The fat removal device of claim 1, wherein a negative pressure is provided to the hollow suction tube, the connection unit, and the pipeline.

8. The fat removal device of claim 1, wherein the microprocessor is connected to the navigation system, the hollow suction tube, the connection unit, the robotic arm, and the suction unit in a wireless or wired manner.

9. The fat removal device of claim 1, wherein the microprocessor further comprises a sensing unit.

10. The fat removal device of claim 9, wherein the sensing unit is a three-dimensional scanner, an ultrasonic detector, a photosensor, a thermal sensor, a camera, or the like, to provide signals to the microprocessor.

11. The fat removal device of claim 1, wherein the robotic arm moves multidirectionally in the latitudinal, longitudinal, and transverse directions.

* * * * *